(12) United States Patent
Valdez et al.

(10) Patent No.: US 10,112,912 B2
(45) Date of Patent: Oct. 30, 2018

(54) HOMOPIPERAZINE-BASED CATALYSTS FOR NEUTRALIZATION OF ORGANOPHOSPHORUS-BASED COMPOUNDS

(71) Applicant: Lawrence Livermore National Security, LLC, Livermore, CA (US)

(72) Inventors: Carlos Valdez, San Ramon, CA (US); Edmond Y. Lau, Dublin, CA (US); Brian P. Mayer, San Francisco, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/059,232

(22) Filed: Mar. 2, 2016

(65) Prior Publication Data
US 2017/0253568 A1 Sep. 7, 2017

(51) Int. Cl.
| | |
|---|---|
| C07D 249/04 | (2006.01) |
| C07D 249/06 | (2006.01) |
| B01J 31/18 | (2006.01) |
| B01J 31/02 | (2006.01) |
| B01J 31/06 | (2006.01) |
| A01N 25/32 | (2006.01) |
| C07D 243/08 | (2006.01) |

(52) U.S. Cl.
CPC ........... *C07D 249/06* (2013.01); *A01N 25/32* (2013.01); *B01J 31/0237* (2013.01); *B01J 31/06* (2013.01); *B01J 31/182* (2013.01); *C07D 243/08* (2013.01); *C07D 249/04* (2013.01); *B01J 2531/16* (2013.01); *B01J 2531/26* (2013.01); *B01J 2531/842* (2013.01); *B01J 2531/845* (2013.01); *B01J 2531/847* (2013.01)

(58) Field of Classification Search
CPC ............................ C07D 243/08; C07D 249/04
USPC .................................................. 540/541, 575
See application file for complete search history.

(56) References Cited

U.S. PATENT DOCUMENTS

| | | | | |
|---|---|---|---|---|
| 5,663,333 A * | 9/1997 | Hodge | ................. | C07D 243/08 540/484 |
| 6,274,051 B1 * | 8/2001 | Cronce | ................... | C02F 1/683 210/753 |
| 6,472,386 B1 * | 10/2002 | Kodama | .............. | C07D 231/12 514/211.08 |
| 7,091,196 B2 * | 8/2006 | Wang | ...................... | A61K 31/42 514/183 |
| 2017/0240569 A1 | 8/2017 | Valdez et al. | | |

FOREIGN PATENT DOCUMENTS

WO    WO 2009/095394    * 8/2009

OTHER PUBLICATIONS

Guo et al., Coordination chemistry of heterocycle-functionalized diazamesocycles: tuning the productive NiII complexes through altering the pendants of ligands, Inorganica Chimica Acta, 358, pp. 1887-1896 (2005).*
Du et al., Synthesis, crystal structure and properties of the CuII complex of a tetradentate imidazole-functionalized diazamesocyclic ligand,1,4-bis(N-1-methylimidazol-2-yl-methyl)-1,4-diazacycloheptane, Journal of Molecular Structure, 641, pp. 29-34 (2002).*
Playa et al., Dilazep analogues for the study of equilibrative nucleoside transporters 1 and 2 (ENT1 and ENT2), Bioorganic & Medicinal Chemistry Letters, 24, pp. 5801-5804 (2014).*
Valdez et al., U.S. Appl. No. 15/048,921, filed Feb. 19, 2016.
Restriction Requirement from U.S. Appl. No. 15/048,921, dated Apr. 3, 2017.
Non-Final Office Action from U.S. Appl. No. 15/048,921, dated Jul. 13, 2017.
Benoist et al., "A Click procedure with heterogeneous copper to tether technetium-99m chelating agents and rhenium complexes. Evaluation of the chelating properties and biodistribution of the new radiolabelled glucose conjugates," Carbohydrate Research, vol. 346, 2011, pp. 26-34.

(Continued)

*Primary Examiner* — Deepak R Rao
(74) *Attorney, Agent, or Firm* — Zilka-Kotab, P.C.

(57) ABSTRACT

Novel compositions of matter based on homopiperazine precursor materials and forming a homopiperazine-based ligand are disclosed, along with suitable techniques and materials for the synthesis and utilization thereof. In particular various synthetic schemes and techniques for applying the disclosed compositions of matter as a decontaminating agent. The decontaminating agents include homopiperazine-based ligand-metal complexes that are particularly effective at neutralizing toxicity of nerve agents, pesticides, and other toxic organophosphorus-based compounds. In preferred approaches, the homopiperazine-based ligand-metal complexes act as catalysts to facilitate substitution of a leaving group of the organophosphorus-based compound with a functional group that does not permit the organophosphorus-based compound to inactivate acetylcholinesterase upon introduction of the organophosphorus-based compound to a living organism such as insects and mammals. Advantageously, the catalytic homopiperazine-based ligand-metal complexes are formed using inexpensive, readily-available precursor materials, and may be utilized to neutralize toxins without relying on damaging caustic reactants or environmentally unfriendly organic solvents.

17 Claims, 13 Drawing Sheets

(56) References Cited

OTHER PUBLICATIONS

Yao et al., "Copper-catalyzed regioselective hydroboration of terminal alkynes in aqueous medium," Tetrahedron Letters, vol. 57, 2016, pp. 910-913.
You et al., "Two multidentate ligands utilizing triazolyl, pyridinyl and phenolate groups as donors for constructing dinuclear copper(II) and iron(III) complexes: Synthesis, structures, and electrochemistry," Inorganica Chimica Acta, vol. 423, 2014, pp. 332-339.
Final Office Action from U.S. Appl. No. 15/048,921, dated Dec. 7, 2017.
Notice of Allowance from U.S. Appl. No. 15/048,921, dated Jul. 30, 2018.

* cited by examiner

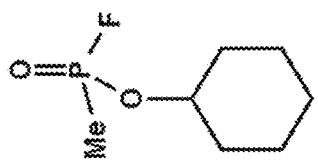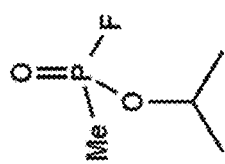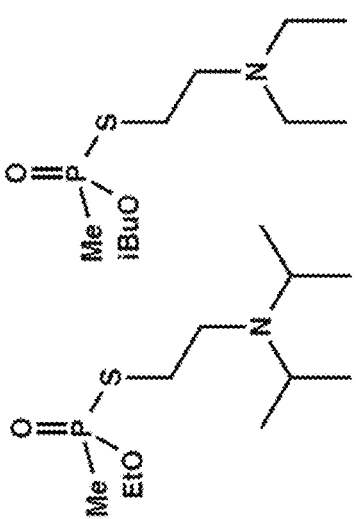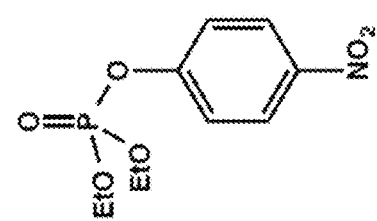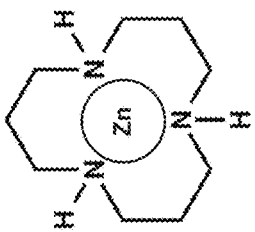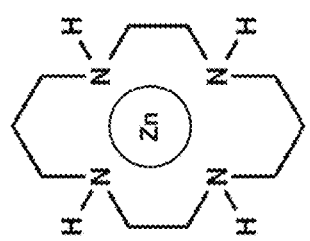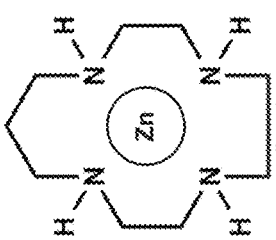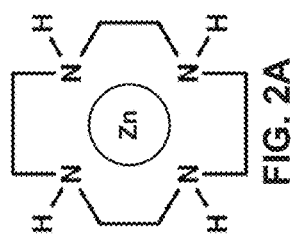

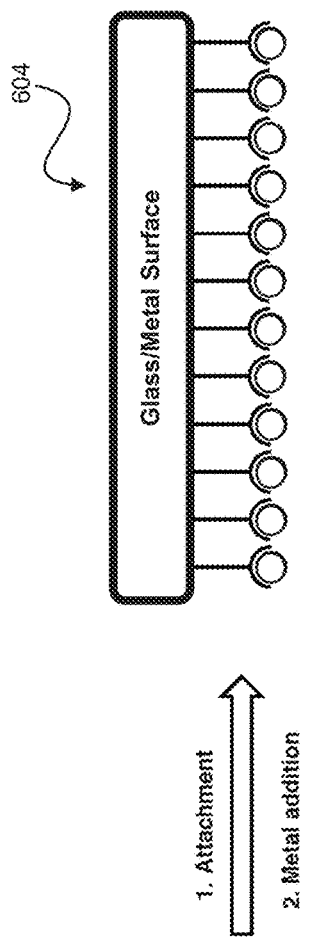
FIG. 6A
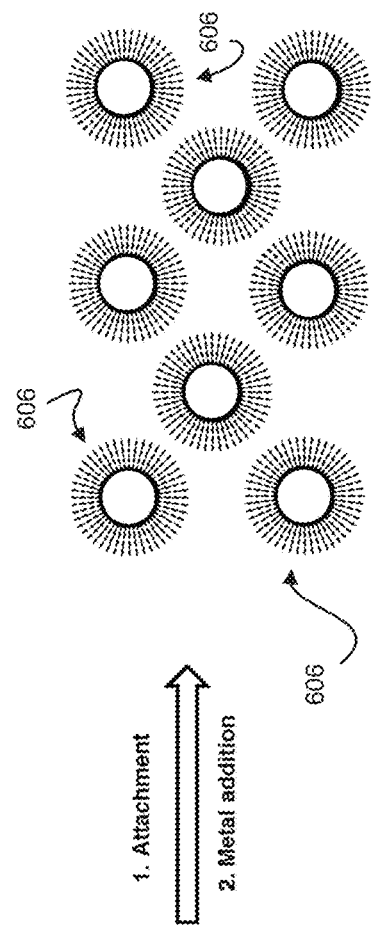
FIG. 6B
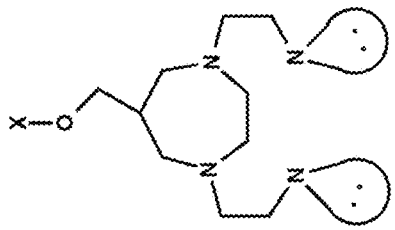
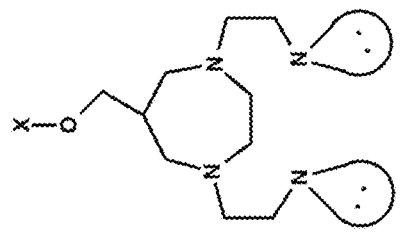

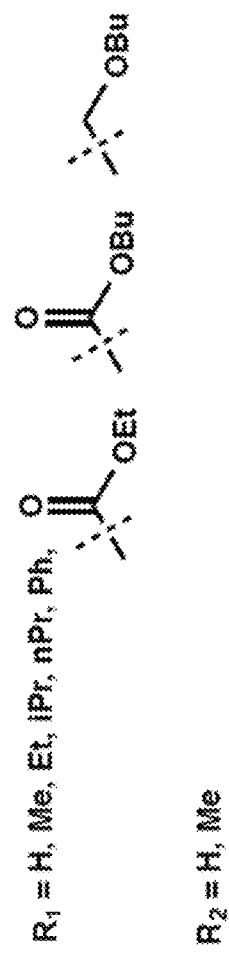
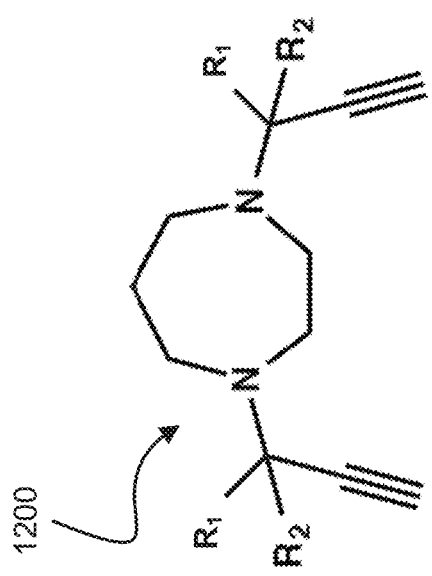
FIG. 12A

HOMOPIPERAZINE-BASED CATALYSTS FOR NEUTRALIZATION OF ORGANOPHOSPHORUS-BASED COMPOUNDS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to homopiperazine-based catalysts, and more particularly, this invention relates to design and use of homopiperazine-based compounds for catalytic destruction of organophosphorus-based compounds such as pesticides and nerve agents.

BACKGROUND

The use of organophosphorus-based compounds as pesticides, solvents, and plasticizers is well-known and effective in the intended capacity. However, persistence of these compounds in the environment leads to adverse collateral impact, and several known organophosphorus-based compounds are acutely toxic nerve agents to insects and humans. The adverse effects are compounded by the fact that these organophosphorus-based compounds are highly toxic even at low doses, capable of being absorbed through skin, and very fast-acting.

In particular, toxicity of organophosphorus-based compounds arises from a structural motif characterized by an electrophilic phosphorous oxide center in which the phosphorous atom is bonded to one or more, typically three, substituents, one of which is capable of acting as a leaving group.

Exemplary toxic organophosphorus-based compounds shown in FIGS. 1A-1E include paraoxon (diethyl 4-nitrophenyl phosphate), V-series agents such as VX (O-ethyl S-[2-(diisopropylamino)ethyl]methylphosphonothioate), VR (N,N-diethyl-2-(methyl-(2methylpropoxy)phosphoryl) sulfanylethanamine), G-series agents such as sarin gas ((RS)-propan-2-yl methylphosphonofluoridate), and cyclosarin (cyclohexyl methylphosphonofluoridate).

In vivo, the leaving group of the organophosphorus-based compound departs and the compound irreversibly inactivates the acetylcholinesterase enzyme, disrupting the nervous system's ability to modulate muscular contractions. Disruption of smooth muscle tissue in the respiratory system leads to rapid death upon exposure to these toxic organophosphorus-based compounds, even at very low dosages.

Several existing techniques for inactivating or otherwise neutralizing organophosphorus-based compounds have been proposed, but generally rely on using excessive amounts of highly caustic agents such as bleach, sodium hydroxide and/or potassium hydroxide (e.g. pH≥12), which tends to damage or destroy the material to which the neutralizing agent is applied. Existing catalytic approaches rely on excessive amounts of organic solvents such as alcohols to accomplish neutralization, as well as rare and/or expensive catalysts including iridium, platinum, and/or palladium. Conventional catalytic approaches have also been troubled by a tendency for the catalyzed products to subsequently react with the catalyst, inhibiting or destroying catalytic capabilities. Particularly when using such expensive metals as catalysts, this inhibition further reduces efficiency of the overall neutralization process and exacerbates the expense of accomplishing effective neutralization. As such, the conventional techniques are expensive, and cause extensive collateral damage to the treated materials and/or the environment (e.g. where the organophosphorus-based compounds are employed as pesticides).

Accordingly, it would be of significant environmental and economic benefit to provide novel, freely available, and inexpensive materials, synthetic techniques, and deployment methods for the destruction of organophosphorus-based compounds.

SUMMARY

In one embodiment, a composition of matter includes a homopiperazine-based ligand.

In another embodiment, a method of forming homopiperazine-based catalysts includes reacting a homopiperazine-based compound with one or more of an azide and a terminal alkyne in the presence of Cu(I) to form a library of homopiperazine-based ligands.

In yet another embodiment, a method includes neutralizing toxicity of one or more organophosphorus-based compounds by reacting the organophosphorus-based compound(s) with a homopiperazine-based ligand-metal complex.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

FIGS. 1A-1E depict simplified schematics of exemplary organophosphorus-based compounds suitable for degradation catalyzed by the presently disclosed inventive homopiperazine-based compounds, according to various embodiments.

FIGS. 2A-2D depict simplified schematics of several known zinc-based catalysts that do not employ homopiperazine-based compounds.

FIG. 6A depicts a simplified reaction scheme for functionalizing a substrate with the presently disclosed homopiperazine-based catalysts, according to one embodiment of the presently disclosed inventive concepts.

FIG. 6B depicts a simplified reaction scheme for functionalizing particles with the presently disclosed homopiperazine-based catalysts, according to another embodiment of the presently disclosed inventive concepts.

FIG. 12A depicts alternative intermediate chemical structures suitable for homopiperazine-based ligand synthesis, according to one embodiment of the presently disclosed inventive concepts.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The presently disclosed inventive concepts are directed to homopiperazine-based catalysts suitable for use in neutralizing the toxicity of organophosphorus-based compounds, as well as the synthesis and utilization thereof.

Advantageously, the presently disclosed materials, methods of synthesis, and implementations of homopiperazine-based catalysts relies on cheap, highly-available materials (both regarding the catalytic metal cations and the organic ligands) as well as simple, high-yield synthetic techniques. This approach confers significant economic advantage to the process of neutralizing toxicity of organophosphorus-based compounds compared to conventional approaches.

In addition, the presently disclosed homopiperazine-based catalysts and implementations thereof accomplish neutralization of toxic organophosphorus-based compounds without relying on caustic agents such as bleach, high-pH materials such as sodium or potassium hydroxide solutions; or organic solvents such as alcohols. Rather, the presently disclosed homopiperazine-based catalysts may carry out neutralization using only water as an intermediary, e.g. to provide a hydroxyl moiety to substitute for a leaving group of the organophosphorus-based compound, and optionally to carry away cleaved leaving group moieties and/or neutralized organophosphorus-based compounds from a substrate being treated. Accordingly, the presently disclosed inventive concepts are characterized by facile deployment using only environmentally friendly materials such as water to facilitate neutralization.

Thus, in one general embodiment, a composition of matter includes a homopiperazine-based ligand.

In another general embodiment, a method includes reacting a homopiperazine-based compound with one or more of an azide and a terminal alkyne in the presence of Cu(I) to form a library of homopiperazine-based ligands.

In yet another general embodiment, a method includes neutralizing toxicity of one or more organophosphorus-based compounds by reacting the organophosphorus-based compound(s) with a homopiperazine-based ligand-metal complex.

Figure 5:
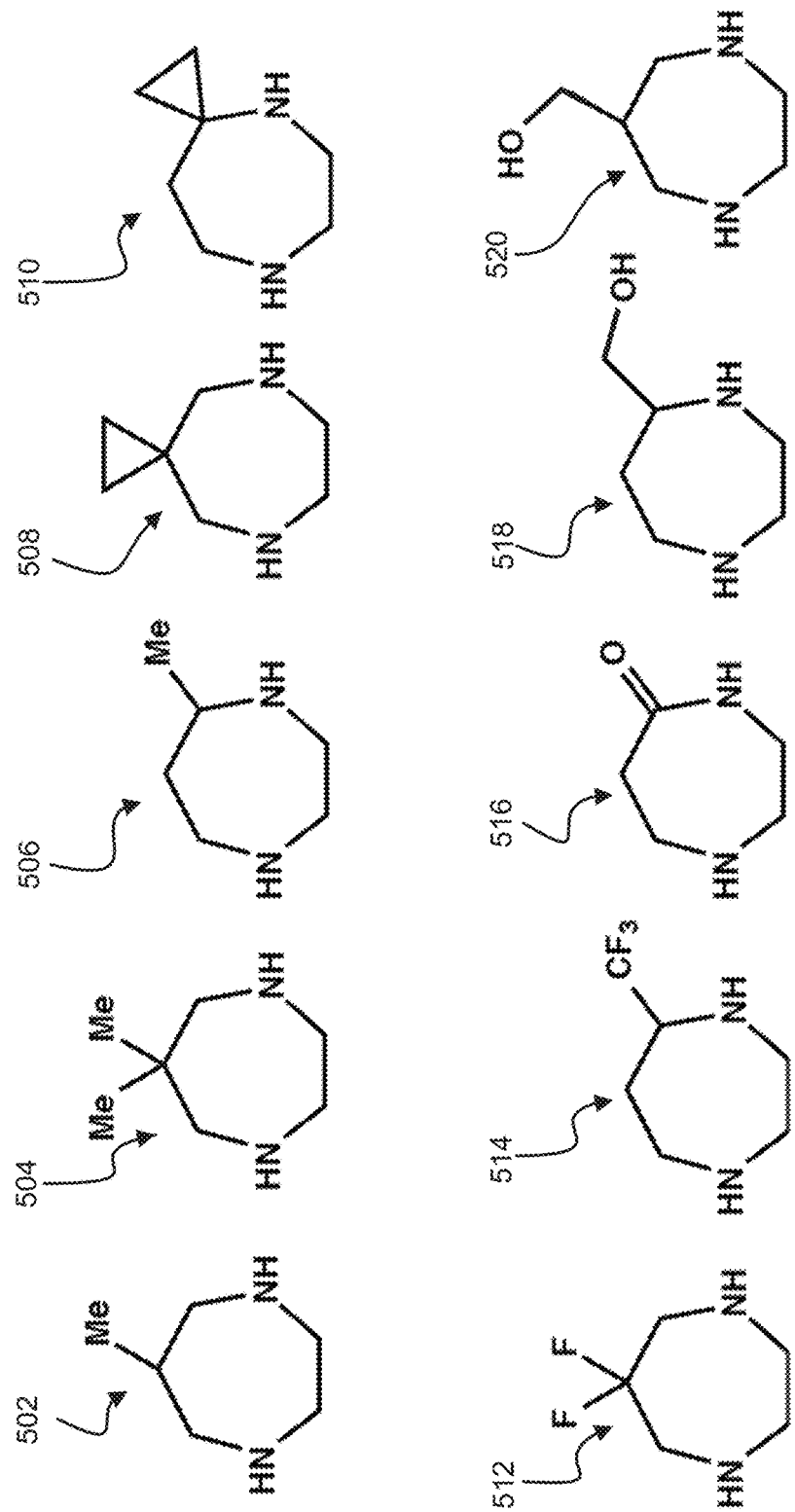
FIG. 5 depicts a plurality of homopiperazine-based precursor materials suitable for use in synthesizing homopiperazine-based ligands and catalysts, according to one embodiment of the presently disclosed inventive concepts.

Homopiperazine-based compounds, as disclosed herein and examples of which include homopiperazine-based compounds 502-520 as depicted in FIG. 5, are suitable for use in generating libraries of organic ligands capable of chelating a metal cation. In particular, multiple nitrogen atoms of homopiperazine-based compounds have been discovered to strongly bind metal cations, allowing subsequent formation of a complex between the chelated metal cation and a water molecule. Advantageously, these homopiperazine-based compounds chelate the metal cation with sufficient strength to prevent subsequent inhibition of the catalytic activity, e.g. due to reaction or complexation with products of the catalysis. Moreover, the homopiperazine-based ligands disclosed herein are preferably characterized by a high degree of structural integrity and rigidity, such that the compounds may retain their structure even when subjected to temperatures sufficient to boil water (100 C).

Similar activity has been demonstrated for cyclic [12-14]ane-N[3-4] compounds, such as shown in FIGS. 2A-2D. For these compounds, upon complexation to the metal cation, the water molecule becomes significantly more acidic than when unbound, e.g. undergoing a change in $pK_a$ from about 15.7 to a $pK_a$ in a range from about 6.0-10.0. This increased acidity of the bound water molecule catalyzes various reactions with other molecules. However, the synthesis of these cyclic catalysts is cumbersome, inefficient, and costly in comparison to the synthesis of the inventive homopiperazine-based compounds disclosed herein.

In addition, the homopiperazine-based compounds disclosed herein are expected to provide superior catalytic activity for the neutralization of toxicity in organophosphorus-based compounds, at least in part due to the open nature of the structure, which facilitates binding of the metal cation and subsequent catalysis of substitution reactions with organophosphorus-based compounds.

In the case of homopiperazine-based compounds as disclosed herein, the increased acidity facilitates catalysis of organophosphorus-based compounds. In particular, reacting the presently disclosed homopiperazine-based catalysts with an organophosphorus-based compound effectively neutralizes the toxicity of the organophosphorus-based compound by substituting a hydroxyl moiety for the leaving group of the organophosphorus-based compound. Thus, in preferred approaches the presently disclosed inventive homopiperazine-based catalysts, when conjugated with a water molecule, preferably exhibit a pKa with respect to the water molecule in a range from about 6.0 to about 10.0, more preferably from about 6.5 to about 8.1. As utilized herein, the term "about" should be understood to encompass±10% of the stated value(s).

Figure 3A:
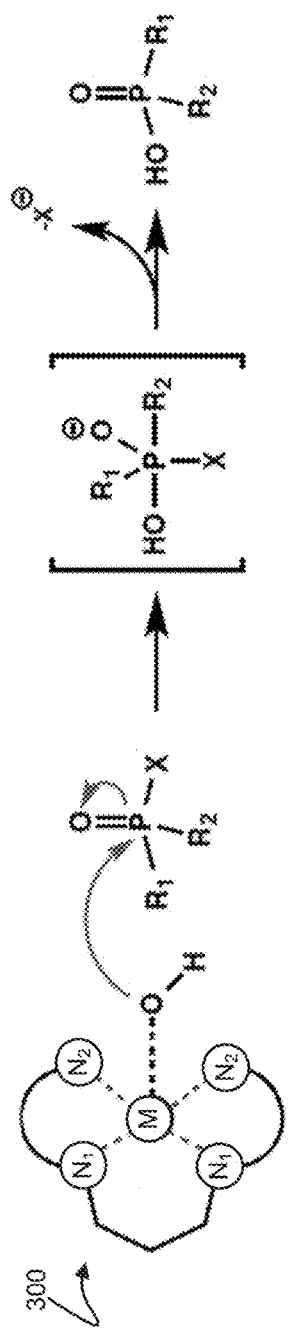
FIG. 3A depicts an exemplary reaction scheme by which the presently disclosed inventive homopiperazine-based compounds may catalyze organophosphorus-based compounds and effectively neutralize the toxicity thereof, according to one embodiment.
Figure 3B:
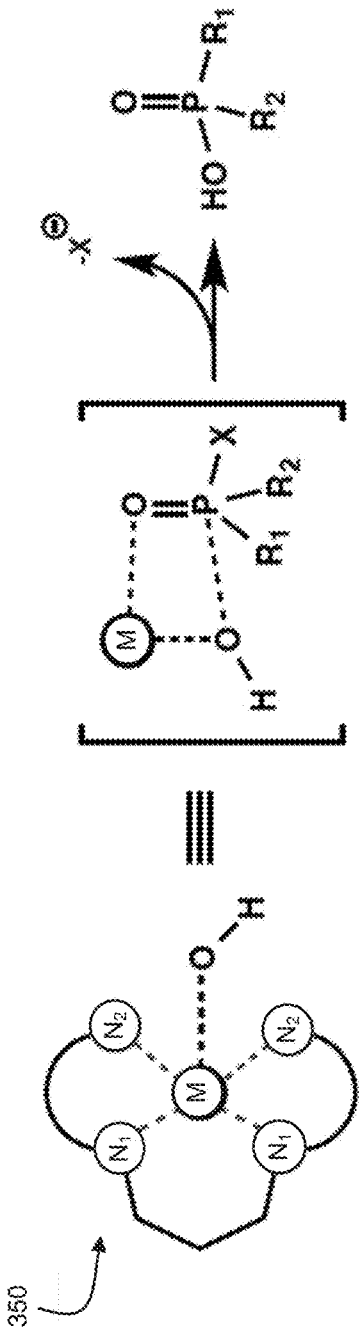
FIG. 3B depicts an exemplary reaction scheme by which the presently disclosed inventive homopiperazine-based compounds may catalyze organophosphorus-based compounds and effectively neutralize the toxicity thereof by substituting a leaving group of the organophosphorus-based compound with a hydroxyl moiety, according to another embodiment.

Exemplary mechanisms for this reaction scheme are depicted in FIGS. 3A-B, according to alternative embodiments. There are two proposed pathways for the function of the presently disclosed homopiperazine-based compounds. Scheme 300 involves a bimolecular reaction with the direct transfer of the hydroxide ion to the P-center with concomitant expulsion of the organophosphorus-based compound's best leaving group. Thus, in the case of paraoxon (FIG. 1A), the leaving group is expected to be the nitrophenolate ion (pKa of conjugate acid=7.1), while for the G-series (FIGS. 1D-1E) and the V-series (FIGS. 1B-1C) agents it is expected to be the fluoride ion (pKa of conjugate acid=3.2) and the thiolate anion (pKa of conjugate acid=8.6) respectively.

Reaction scheme 350, shown in FIG. 3B, involves another bimolecular reaction but with a previous, ordered coordination of the metal center with the oxygen atom of the P=O region of the organophosphorus based compound. As in the first proposed mechanism, once the coordination has occurred, the hydroxide ion is transferred from the complex to the agent with concomitant departure of the leaving group. Even though it is expected that in all these proposed mechanisms, it should be the best leaving group departing every time the catalyst encounters the agent (i.e. the arm with the lowest pKa value), this is not always the case.

For instance, other groups in the organophosphorus-based compounds may leave as well, as in the case of paraoxon, where products were formed from the departure of both the nitrophenolate ion and the unexpected ethoxide ion. This observation, of course, points towards the fact that there could be an intermediate at play during these reactions, and since the phosphorus-center can accommodate extra substituents to form trigonal bipyramidal structures, then it is postulated that anti-orientation of the entering hydroxide ion and the leaving group plays a small role indeed.

Figure 4A:
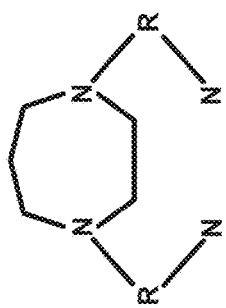
FIG. 4A depicts a simplified schematic of a central chelating site of the presently disclosed inventive homopiperazine-based compounds by substituting a leaving group of the organophosphorus-based compound with a hydroxyl moiety, according to one embodiment.
Figure 4E:
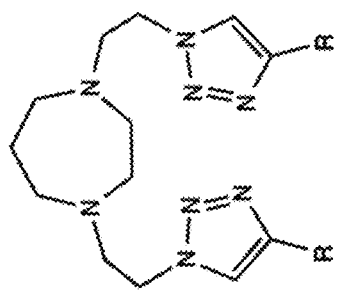
FIGS. 4B-4E depict simplified schematics of exemplary homopiperazine-based compounds, according to one embodiment of the presently disclosed inventive concepts.
Figure 4D:
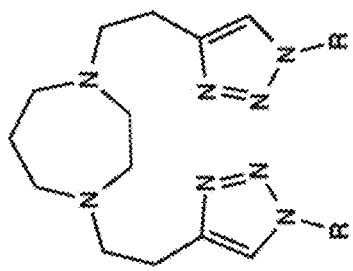
Figure 4C:
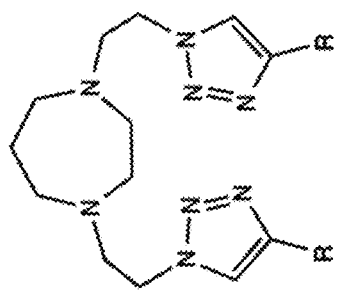
Figure 4B:
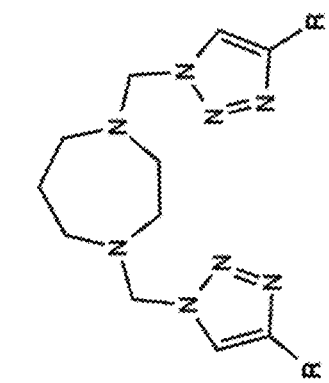

Thus, the following invention describes a novel series of nitrogen-containing ligands, optionally joined by a fully saturated 1,4-diazepine nucleus, that are capable of coordinating different metal ions. The inventive compounds are preferably characterized by a structure substantially as shown in FIG. 4A, with four nitrogen atoms available to participate in conjugating the metal cation in the central region therebetween. The R groups of the structure shown in FIG. 4A may be —$CH_2C$—, —$CH_2N$—; —$CH_2CH_2C$—; or —$CH_2CH_2N$—, in various embodiments. Of course, other equivalent R groups that would be appreciated by a skilled artisan upon reading the present descriptions should be considered within the scope of these inventive concepts.

The structures of particularly preferred embodiments of homopiperazine-based ligands as disclosed herein are shown in FIGS. 4B-4E, again according to various illustrative embodiments. The R groups depicted may be selected based on the manner in which the homopiperazine-based ligand is to be employed, e.g. to confer additional advantageous functionality such as an electron donating group to facilitate binding of the metal cation, electron withdrawing groups to modulate the length of the Zn—$OH_2$ bond (by shortening or lengthening it) and thus directly affect the pKa of the attached water molecule that may result in an increase nucleophilicity and thus, activity of the complex, according to preferred embodiments, a solubilizing ligand such as polyethylene glycol to tune solubility of the homopiperazine-based compound to be compatible with a suitable solvent, buffer composition, etc. as would be understood by a person having ordinary skill in the art upon reading the present descriptions.

For instance, in various embodiments a suitable solvent is preferably water, but may also include organic phase solvents, peroxides, salts, etc. as would be understood by a person having ordinary skill in the art upon reading the present descriptions. In addition, the solvent preferably has a pH in a range from about 7.0 to about 7.4 to facilitate substitution mediated by the homopiperazine-based catalysts. In addition, the active catalyst is preferably loaded in the buffer, solvent, etc. in a particular molar ratio with respect to the amount of agent to be neutralized. In preferred approaches, the decontamination solution preferably is loaded with homopiperazine-based catalyst in an amount ranging from about 10 mol % to about 50 mol % with respect to the organophosphorus-based compound to be neutralized.

Figure 12B:
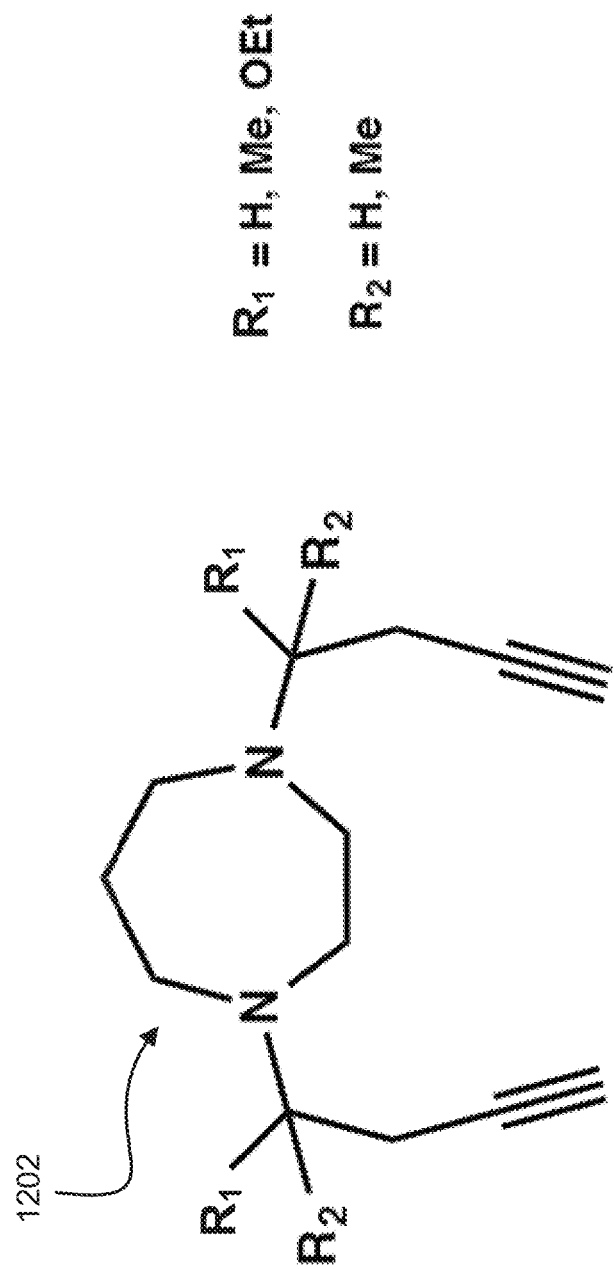
FIG. 12B depicts alternative intermediate chemical structures suitable for homopiperazine-based ligand synthesis, according to one embodiment of the presently disclosed inventive concepts.

Of course, other structures than those shown in FIGS. 4B-4E and modifications to the structures shown in FIGS. 4B-4E may be employed without departing from the scope of the present disclosures, with the limitation that the structures and modifications retain catalytic capability to neutralize organophosphorus-based compounds. Exemplary modifications expressly contemplated include addition of a chemical handle at the C(6) or C(7) position of the homopiperazine ring with a hydroxymethyl moiety, e.g. as shown in structures 518 and 520, depicted in FIG. 5, as well as modifications arising from using different intermediate structures, e.g. 1200 and/or 1202 as depicted in FIGS. 12A-12B.

Presence of the a chemical handle such as a hydroxymethyl moiety provides an additional handle to further modify the molecule in order to modulate its physical properties (e.g. water solubility, lipophilicity, c log P value, surface area, etc. as would be understood by a person having ordinary skill in the art upon reading the present descriptions). In addition, due to this additional reactive group, the complexes arising from such scaffolds can be easily and efficiently attached to surfaces (e.g. glass, metal, Au or Ag nanoparticles, etc. as would be understood by a person having ordinary skill in the art upon reading the present descriptions) or solid supports (e.g. polystyrene-based resin, controlled pore glass beads, a polymeric or fibrous filter, matrix, etc. as would be employed e.g. in respiratory equipment, etc. as would be understood by a person having ordinary skill in the art upon reading the present descriptions).

Attachment of these complexes, e.g. to solid supports 606 or surfaces 604, as shown in FIGS. 6A and 6B, allows for the development of materials with the capability of capturing and decontaminating organophosphorus-based nerve agents. Other functionalities stemming from the homopiperazine scaffold can be used as well for these conjugative applications such as amines and thiols.

In various approaches, the presently disclosed inventive homopiperazine-based ligands and catalytic complexes may be employed using a variety of solvents, buffers, etc. and preferably environmentally friendly solvents, buffers, etc. as would be understood by a person having ordinary skill in the art upon reading the present descriptions.

Turning now to synthesis, advantageously these ligands can be assembled in 3-4 steps from readily, commercially-available and inexpensive homopiperazine (also known as 2,3,4,5,6,7-hexahydro-1H-1,4-diazepine), and/or modified homopiperazine analogs, such as shown in FIG. 5, in various embodiments. One of the strongest aspects of this approach is the fact that a myriad of analogs displaying different chemical, reactive and structural properties can be accomplished using the Cu(I)-catalyzed azide-alkyne cycloaddition reaction ("CuAAC" or "click chemistry"). Complexation of these ligands to different metal ions opens their application in the areas of organophosphorus-based compound destruction, carbon capture technologies and in the study of triazole-based ligand-metal interactions.

The proposed ligands can be synthesized using homopiperazine and analogs thereof as the starting material, including any of the exemplary modified homopiperazine compounds 502-520 as shown in FIG. 5. Homopiperazine is inexpensive and can be purchased in multi-gram quantities making the production of a compound library an economically efficient task. Of course, skilled artisans in the field of synthetic organic chemistry will appreciate that the modified homopiperazine compounds 502-520 shown in FIG. 5 are merely exemplary, and should not be considered limiting on the scope of the presently disclosed inventive concepts. Equivalent modified homopiperazine compounds are also to be considered within the scope of the present invention, as would be understood by a person having ordinary skill in the art upon reading the present descriptions.

Turning now to synthesis of homopiperazine-based ligands, according to various embodiments a variety of synthetic schemes may be employed, e.g. as illustrated in FIGS. 7-10 and described in further detail below. The exemplary synthetic schemes depicted and described herein are characterized by the presence of an intermediate material that can then be used for library production, preferably using Cu(I)-catalyzed azide-alkyne cycloaddition reaction (click chemistry) to generate suitable ligands.

Figure 7:
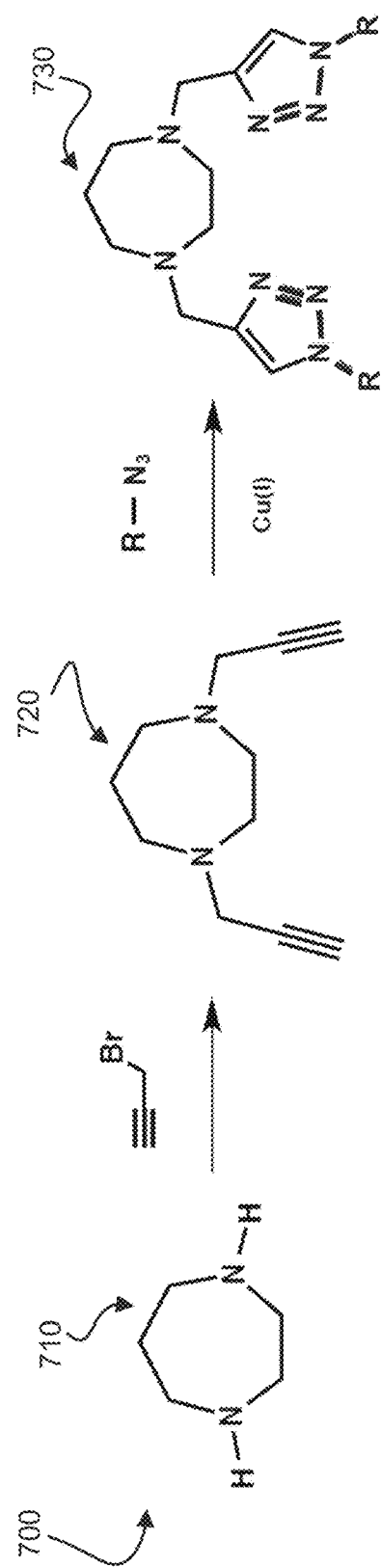
FIG. 7 depicts a simplified reaction scheme for synthesizing bis-triazolyl homopiperazine ligands, according to one embodiment of the presently disclosed inventive concepts.

Thus as shown in FIG. 7, according to one embodiment ligand synthesis scheme 700 involves alkylation of homopiperazine 710 with propargyl bromide to produce a bis-propargylated intermediate 720. Advantageously, this one step sequence provides an intermediate 720 suitable for library production using inexpensive materials and high-yield synthesis, contributing to the economic efficiency of the presently disclosed inventive concepts. The intermediate 720 may then be reacted with a panel of organic azides, preferably using click chemistry, to generate suitable ligands 730, according to one embodiment.

Figure 8:
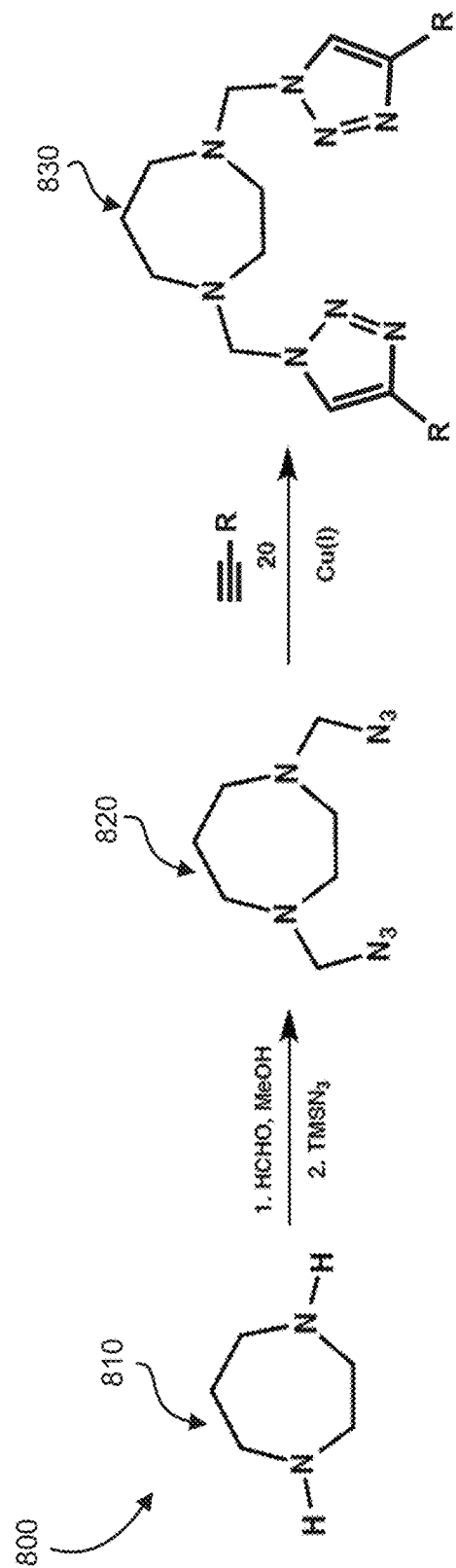
FIG. 8 depicts a simplified reaction scheme for synthesizing bis-triazolyl homopiperazine ligands, according to another embodiment of the presently disclosed inventive concepts.

A synthesis scheme 800 for ligand 830 is depicted in FIG. 8, according to one embodiment, and involves bis-methoxymethylation of homopiperazine or a modified homopiperazine 810 with formaldehyde and methanol to facilitate the direct conversion of these species to a bis-azidomethyl intermediate 820 using trimethylsilyl azide (JACS 2007, 6080-88). Intermediate 820 is the central target that can be reacted with a library of alkyne-based reagents to create a vast library of ligands 830, preferably using click chemistry and according to another embodiment. Again, this simple and high-yield synthetic process using inexpensive starting materials contributes to the economic efficiency of the presently disclosed inventive concepts.

A point of comparison between the creation of libraries from central intermediates 720 and 820 lies in ease of construction. While intermediate 720 requires azides in order for the library to be built, intermediate 820 requires terminal alkynes to do so, according to the embodiments shown in FIGS. 7 and 8. Thus, the latter yields faster, more elaborate libraries, in part due to the fact that terminal alkynes can be simply purchased from commercial vendors. The opposite is true for the library arising from intermediate 720, since the azides must often be synthesized from a respective parent alkyl halide or alcohol via a two-step process. Accordingly, while each technique represents a substantial improvement over conventional catalytic approaches to organophosphorus-based compound catalysis, scheme 800 as depicted in FIG. 8 represents a particularly significant advantage in this regard.

Figure 9:
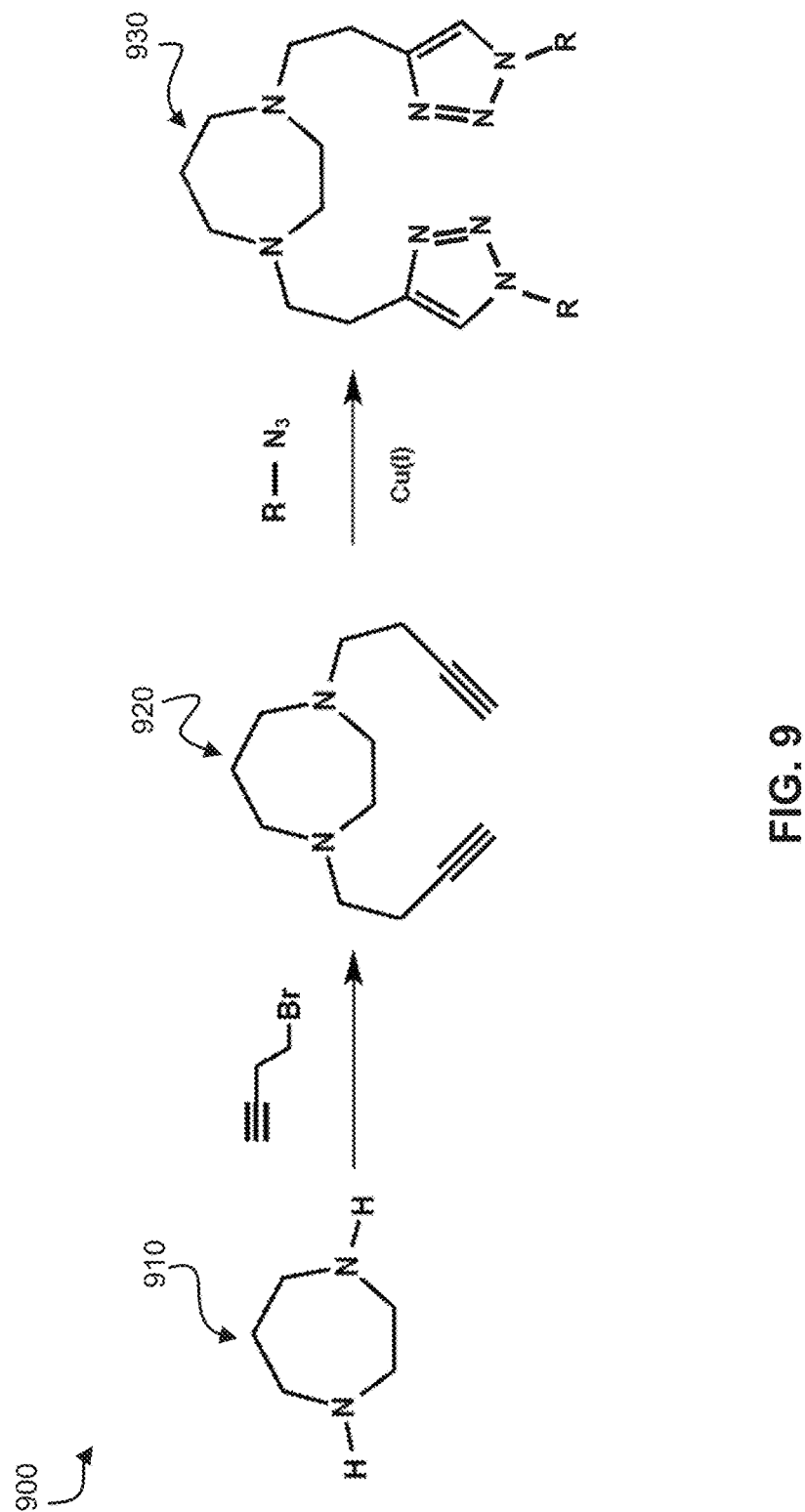
FIG. 9 depicts a simplified reaction scheme for synthesizing bis-triazolyl homopiperazine ligands, according to yet another embodiment of the presently disclosed inventive concepts.

Referring now to FIG. 9, the synthesis scheme 900 of ligand 930 is similar to that of 430, according to one embodiment. In place of propargyl bromide, homopropargyl bromide is reacted with precursor 910. Again, a bis-alkynyl is obtained as an intermediate compound 920 used for library construction. Treatment of the intermediate 920 with a panel of azide-containing compounds in the presence of Cu(I) provides a library of bis-triazolyl ligands.

Figure 10:
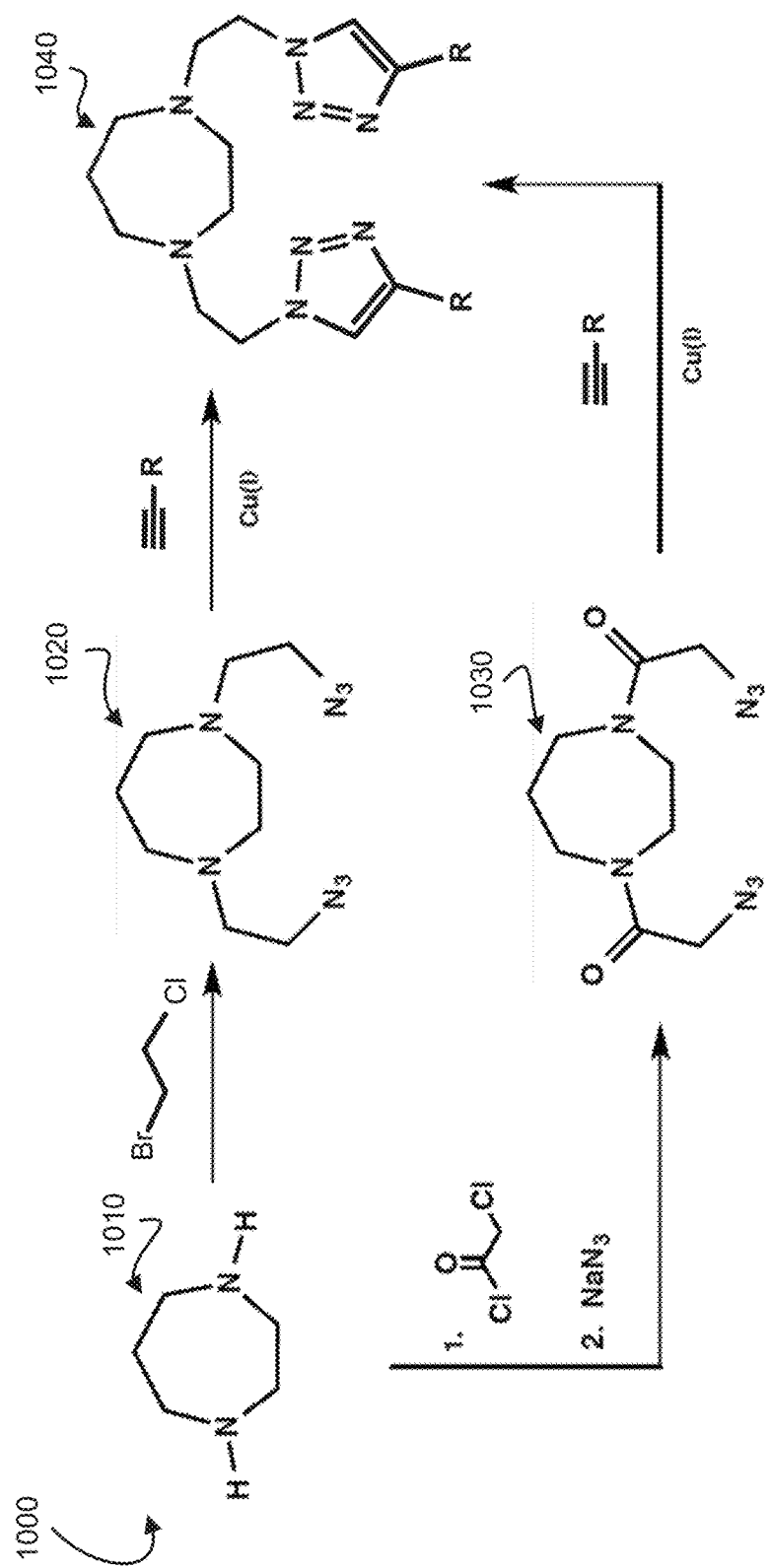
FIG. 10 depicts a simplified reaction scheme for synthesizing bis-triazolyl homopiperazine ligands, according to still yet another embodiment of the presently disclosed inventive concepts.

Turning to FIG. 10, the synthesis scheme 1000 of ligand 1040 is outlined, according to one embodiment. The synthesis can be accomplished using two preferred pathways. In the upper scheme shown in FIG. 10, alkylation of homopiperazine or a modified homopiperazine 1010 with 1-bromo-2-chloroethane is followed by displacement of the bromines to give a bis-azidoethylhomopiperazine intermediate 1020. Reaction of the intermediate 1020 with alkyne bearing compounds in the presence of Cu(I) yields triazole ligands 1040, according to one embodiment.

The second pathway involves the reaction of homopiperazine or a modified homopiperazine 1010 with chloroacetyl chloride followed by NaN$_3$ to give the bis-α-azido-acetylamidohomopiperazine intermediate 1030. Reaction of the intermediate 1030 with a panel of terminal-alkyne bearing compounds in the presence of Cu(I), followed by conventional amide reduction yields the desired ligand 1040, according to another embodiment.

Of course, the synthetic pathways shown in FIGS. 7-10 may also include additional steps (not shown) such as precursor reactions required to generate the reactants shown in FIGS. 7-10 using precursor materials. Preferably, the synthesis may be carried out in a simple two-step scheme as shown in FIGS. 7-10, but where starting materials depicted therein are not readily available they may be separately synthesized without departing from the scope of the present disclosure.

Figure 11:
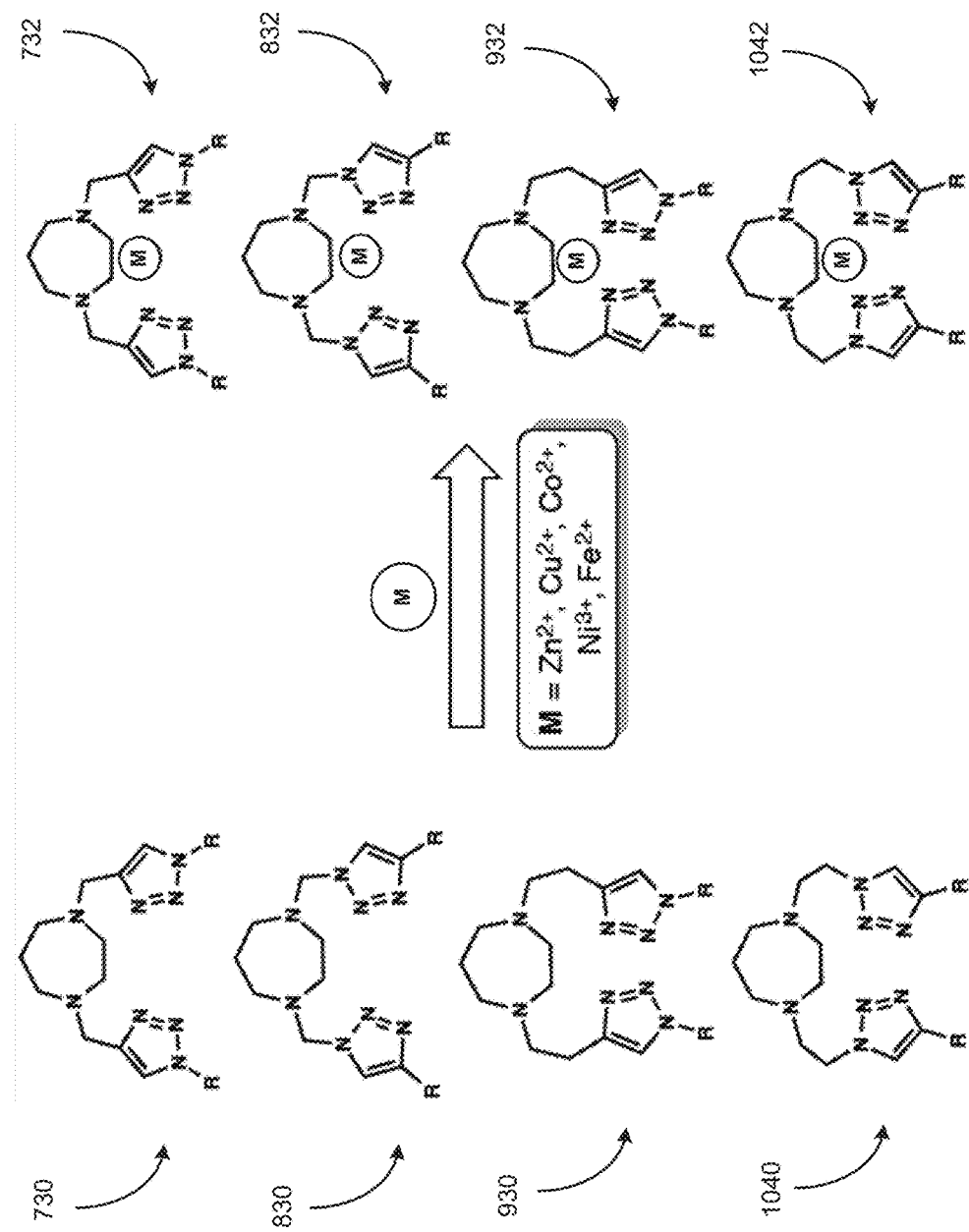
FIG. 11 depicts a simplified reaction scheme for complexing bis-triazolyl homopiperazine ligands with a metal to form homopiperazine-based catalysts, according to one embodiment of the presently disclosed inventive concepts.

Following synthesis, ligands 730, 830, 930, and/or 1040 are preferably complexed with a metal cation to form catalytic ligand-metal complexes 732, 832, 932, and/or 1042, in various embodiments and as shown in FIG. 11. Preferably, complexation includes mixing the ligand and a metal salt in equimolar amounts in an appropriate solvent, such as methanol. Notably, after complexation, the ligand-metal complex may be removed from solution, and subsequently carry out catalytic activity without relying on organic solvents such as alcohols, caustic agents such as bleach, sodium hydroxide, potassium hydroxide, etc. or other environmentally unfriendly materials as would be understood by a person having ordinary skill in the art upon reading the present descriptions.

Rather, the presently disclosed ligand-metal complexes utilize hydrolytic substitution of a hydroxyl moiety (which may be obtained from a water molecule) for the leaving group of the organophosphorus-based compound, and therefore may carry out catalysis using only environmentally friendly materials such as water to facilitate the catalysis. In various embodiments, humidity of the atmosphere may be sufficient to facilitate the ligand-metal complex mediated catalysis.

In multiple embodiments, different sections of the ligand scaffold may be modified to yield a library of compounds. For instance, in one embodiment, the alkyne or azide that is used for the reaction with each one of the key intermediates (boxed central intermediate) in the synthetic schemes shown in FIGS. 7-10 may be modified. In another embodiment, modifications may take the form of a modified homopiperazine starting material, such as shown in FIG. 5. In yet another embodiment, modifications may be made to add additional R groups to the intermediate structure, the R groups including hydrocarbon chains, esters, ethers, aromatic groups, etc., such as $R_1$ and $R_2$ as shown in FIGS. 12A-12B and as would be understood by a person having ordinary skill in the art upon reading the present descriptions One caveat for this type of modification is that it will work straightforwardly with the bis-alkyne intermediates 720 and 920, due to the commercial availability of the alkynes used to modify the homopiperazine ring. In several approaches modifying group is contained in the alkynyl bromide that is used to generate the intermediate structure 720, 820, 920, 1020 and/or 1030 from the corresponding homopiperazine or modified homopiperazine starting material. The structure of exemplary modified intermediates 1200 and 1202 that can be used for the further expansion of a library are shown in FIGS. 12A-12B, according to one embodiment.

Accordingly, in various approaches the presently disclosed inventive concepts may be embodied according to the foregoing descriptive examples. In preferred approaches, the homopiperazine-based compounds may be embodied as follows.

In one embodiment, a composition of matter includes: a homopiperazine-based ligand. The homopiperazine-based ligand is preferably a bis-triazolyl homopiperazine ligand including at least one $sp^2$ nitrogen atom and at least one sp3 nitrogen atom, more preferably at least two $sp^2$ nitrogen atoms and at least two sp3 nitrogen atoms positioned within the composition of matter in a location suitable to chelate a metal cation placed in proximity with the homopiperazine-based ligand.

Accordingly, the nitrogen atoms form a central chelating site configured to chelate a metal cation placed in the chelating site. The chelating site preferably has a structure substantially as shown in FIG. 4A, 12A or 12B, in various approaches. According to the embodiment depicted in FIG. 4A, —R has a structure selected from: —CH$_2$C—, —CH$_2$N—; —CH$_2$CH$_2$C—; and —CH$_2$CH$_2$N—. As shown in FIG. 12A, $R_1$ has a structure selected from hydrogen, methyl, ethyl, isopropyl, n-propyl, phenyl, an ethyl ester, a butyl ester, and a butyl ether, while $R_2$ has a structure selected from hydrogen and methyl. As shown in FIG. 12B, $R_1$ has a structure selected from hydrogen, methyl and ethyl ether, while $R_2$ has a structure selected from hydrogen and methyl.

The composition of matter may also include a chemical handle, preferably on the C(6) carbon of the homopiperazine ring and comprises a hydroxymethyl group. The hydroxymethyl group may be activated with a reactive functionalization motif, preferably one or more of: thiol, hydroxyl, —NH—NH$_2$; and —Si(OR)$_3$.

In more embodiments, a metal cation is conjugated with the homopiperazine ligand to facilitate catalysis of organophosphorus-based compounds. Accordingly, a water or a hydroxyl moiety is preferably functionalized to the metal cation to facilitate the catalysis. In various approaches, the metal cation may be one or more of: $Cu^{2+}$, $Zn^{2+}$, $Co^{2+}$, $Fe^{2+}$, and $Ni^{3+}$.

In still further embodiments, the composition of matter may be functionalized on a substrate embodied as one or more of a surface and a solid support. The surface is preferably one or more of a planar surface and nanoparticles; and the solid support is preferably one or more of porous beads, a resin, a matrix, and a filter.

In still more embodiments, the presently disclosed inventive concepts include techniques for synthesizing and utilizing the aforementioned homopiperazine-based ligands. For instance, an exemplary method 1300 of forming homopiperazine-based ligands according to one embodiment is shown in FIG. 13, while an exemplary method 1400 for employing homopiperazine-based catalysts to neutralize toxicity of organophosphorus-based compounds is shown in FIG. 14.

In various embodiments, the methods 1300 and 1400 may be practiced using any suitable materials disclosed herein, and/or proceed according to any suitable reaction scheme, application technique, etc. each as would be understood by a person having ordinary skill in the art upon reading the instant disclosures. Other equivalent reaction schemes, materials, application techniques, etc. that would be understood by a person having ordinary skill in the art upon reading these disclosures may also be employed without departing from the scope of the inventive concepts presented herein.

Figure 13:
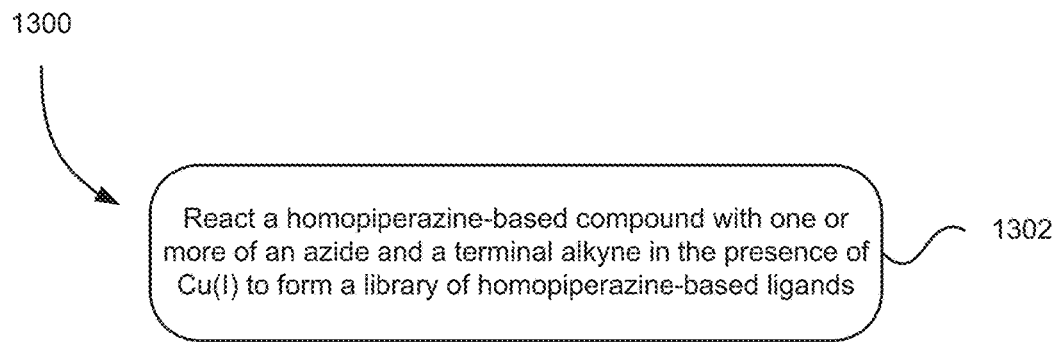
FIG. 13 depicts a flowchart of a method for forming homopiperazine-based ligands, according to one embodiment.
Figure 14:
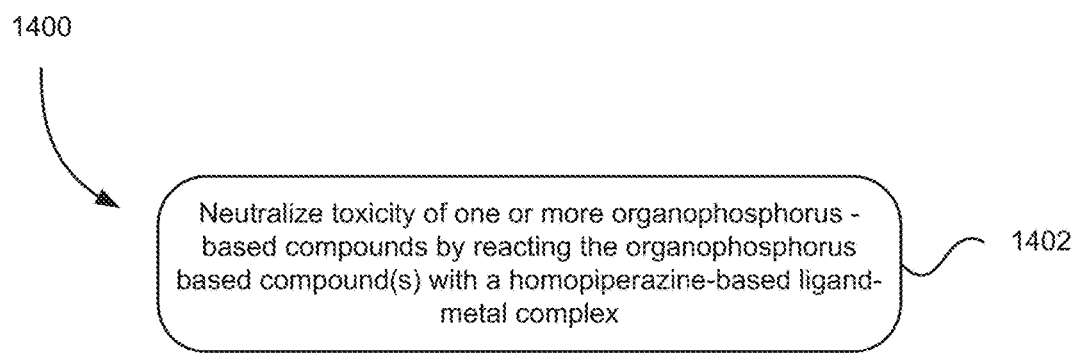
FIG. 14 depicts a flowchart of a method for neutralizing toxicity of organophosphorus-based compounds using homopiperazine-based catalysts, according to one embodiment.

Turning now to FIG. 13, a method 1300 for forming homopiperazine-based ligands is shown, according to one embodiment. The method 1300 may employ any suitable starting materials, e.g. as shown in FIG. 5, any suitable intermediates, e.g. as shown in FIGS. 7-10 and 12A-12B, and result in any suitable final material(s), such as shown in FIGS. 4B-4E, and 6A-11, in various approaches. Similarly, method 1300 may proceed according to any of the reaction schemes shown in FIGS. 7-10, among other suitable equivalent schemes as would be understood by a person having ordinary skill in the art upon reading the present descriptions.

As shown in FIG. 13 the method includes a single step, reflecting the simplicity of the presently disclosed synthetic schemes and techniques. Specifically, method 1300 includes operation 1302, in which a homopiperazine-based compound is reacted with one or more of an azide and a terminal alkyne in the presence of Cu(I) to form a library of homopiperazine-based ligands. The homopiperazine-based compound is preferably one or more of intermediates 720, 820, 920, 1020, 1030, 1200, or 1202 as shown in FIGS. 7-10 and 12A-12B, but any suitable intermediate that would be appreciated by a skilled artisan, e.g. an intermediate characterized by a structure substantially as depicted in FIG. 4A, may be employed without departing from the scope of the present disclosure, in various embodiments. In more embodiments, the terminal nitrogen depicted in FIG. 4A may be a terminal azide (N$_3$) or terminal alkyne (≡CH).

Of course, the method 1300 may include additional operations, features, etc. without departing from the scope of the present disclosure. For instance, in various embodiment the homopiperazine-based compound may be synthesized using one or more of the homopiperazine-based precursor structures as shown in FIG. 5.

In more approaches, reacting the homopiperazine-based compound with the terminal azide and/or terminal alkyne preferably includes Cu(I)-catalyzed azide-alkyne cycloaddition, or "click chemistry." Utilizing click chemistry advantageously increases the efficiency of the synthesis process, as well as generating a variety of homopiperazine-based compounds with structural variations, permitting investigation into relative advantages of various compounds in various applications.

In still more approaches, method 1300 may include conjugating the homopiperazine-based ligands with one or more metal cations. The metal cations are preferably selected for both catalytic activity and affordability. In various embodiments, the metal cations may be selected from a group consisting of: $Cu^{2+}$, $Zn^{2+}$, $Co^{2+}$, $Fe^{2+}$, and $Ni^{3+}$.

In various embodiments, method 1300 may also include functionalizing the metal cation with a hydroxyl moiety, in order to "activate" the catalyst for neutralizing organophosphorus-based compounds. The functionalization may be accomplished intentionally via employing particular chemistry, or may occur naturally due to environmental conditions, e.g. sufficient humidity, precipitation, submersion in a body of water, etc. as would be understood by a person having ordinary skill in the art upon reading the instant disclosures.

Accordingly, method 1300 may further involve functionalizing the homopiperazine-based ligands, ligand-metal complexes, functionalized ligand-metal complexes, etc. to a substrate. The substrate, in various embodiments, may be a surface, a solid support, etc. such as a planar surface, a three-dimensional surface, nanoparticles, polymers, solid or porous beads (e.g. polymer-based beads, magnetic beads, glass beads, etc.), a resin, a filter, fibers, a matrix, an aerogel, etc. as would be understood by a person having ordinary skill in the art upon reading the present disclosures. Particularly preferred surfaces/supports include filters, beads, magnetic nanoparticles, and polymeric fibers.

Turning now to FIG. 14, a method 1400 for neutralizing toxic agents such as organophosphorus-based nerve agents, pesticides, etc. is shown, according to one embodiment. The neutralization technique involves operation 1402, which includes reacting the homopiperazine-based ligand-metal complex(es) with toxic agents such as organophosphorus-based compounds.

In preferred embodiments, the homopiperazine-based ligand-metal complex(es) act as catalysts to facilitate substitution of a leaving group of the organophosphorus-based compound with a hydroxyl moiety, preferably a hydroxyl moiety conjugated to the metal cation of the homopiperazine-based ligand-metal complex.

In various embodiments, method 1400 may, of course, include additional features and/or operations as disclosed herein, and as would be understood by a person having ordinary skill in the art upon reading the present descriptions. For instance, in various approaches method 1400 may include washing a surface or support to which the homopiperazine-based ligand-metal complexes are functionalized, e.g. to carry away neutralized agent, re-activate the homopiperazine-based ligand-metal complex(es) for subsequent neutralization, etc. as would be understood by a person having ordinary skill in the art upon reading the present disclosures.

In additional embodiments, the reaction may benefit from agitation, stirring, etc., e.g. where the sample to be treated includes a liquid sample or a solid sample submerged in a solution of homopiperazine-based ligand-metal complexes and a suitable solvent/buffer composition. Similarly, where the sample to be treated includes a surface, and particularly a large surface, the reaction may benefit from applying an excess of the homopiperazine-based ligand-metal complex(es) via spraying a solution thereof over the surface.

In embodiments where retrieval of the catalysts is desirable, method 1400 may include applying a magnetic field to the treated sample, solution, environment, etc. to facilitate recovery of homopiperazine-based ligand-metal complex(es) functionalized to magnetic beads. Retrieval may optionally include a step of drying, concentrating (e.g. via centrifugation), washing, etc. the beads and functionalized homopiperazine-based catalysts, as well as eluting the homopiperazine-based ligand-metal complex(es) from the beads using an appropriate solvent. Eluted homopiperazine-based ligand-metal complex(es) may be subsequently functionalized to magnetic nanoparticles, or other surfaces, supports, etc. for re-use or use in a different capacity, e.g. in a filter.

Applications

The presently disclosed inventive concepts, materials, etc. may be advantageously employed in a broad range of applications, forms, and techniques to accomplish neutralization of organophosphorus-based compounds. The capability to present these materials and techniques in a wide variety of forms, e.g. as liquid, functionalized on solid surfaces, functionalized on particulates (especially nanoparticles), as an aerosol, etc. advantageously allow the effective neutralization techniques to be implemented in a wide variety of scenarios in which the toxic organophosphorus-based compounds may be encountered in practice.

For instance, in one approach a body of water may become contaminated with organophosphorus-based compounds, in which case the presently disclosed inventive materials and techniques may be utilized to treat the water, e.g. with either the catalyst itself in its free form, or as mixture in the water, e.g. to disinfect using compounds beyond the scope of the present disclosure, as well as decontaminate the water from organophosphorus-based compounds using compounds as disclosed herein.

To facilitate recovery of the homopiperazine-based catalysts, the presently disclosed materials may be functionalized to a metal surface like magnetic beads for example, and subsequently added to a contaminated solution, body of water, etc. such that the magnetic beads can perform the destruction of the agent present in the water. Upon completion of decontamination, it is possible to retrieve the magnetic beads, and thus the bound catalysts, using a magnet. This approach advantageously avoids contaminating the treated sample, surface, solution, etc. with the homopiperazine-based catalysts, which may be useful if the homopiperazine-based catalysts themselves are undesirable for the intended purpose/use of the sample, surface, solution, etc.

Similarly, in various approaches other substrate materials may be employed, such as glass beads, polymer fibers, matrices, etc. as would be understood by a person having ordinary skill in the art upon reading the present descriptions.

In even more approaches, particular metals such as gold for example may be employed as a substrate material. For instance, gold may be particularly advantageous as a substrate material where a thiol group may be cleaved from the organophosphorus-based compound (or otherwise generated in the course of neutralization). Since thiol groups have a strong affinity for gold, using gold as the substrate material may encourage free thiols to bind/complex with the gold rather than attempting to complex with the metal cation catalyzing the substitution reaction. In this manner, inhibitory effects caused by products of the intended catalysis may be mitigated or avoided, in various approaches.

Similarly, from an academic perspective gold or other suitable metals may be useful in the context of enabling investigation of the inventive homopiperazine-based ligands, and their activity, e.g. via Raman spectroscopy.

In more approaches, the presently disclosed inventive homopiperazine-based catalysts may be functionalized on armor panels to provide protection against chemical agent deployment to military personnel, law enforcement, emergency service personnel, etc. as would be understood by a person having ordinary skill in the art upon reading the present disclosures.

Accordingly, the presently disclosed inventive homopiperazine-based catalysts may be embodied as a spray solution, an aerosol, etc. to facilitate rapid and facile application to contaminated surfaces, samples, etc.

In more approaches, the presently disclosed inventive homopiperazine-based catalysts may be embedded it into filters.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A composition of matter, comprising: a homopiperazine-based ligand; wherein the composition of matter has a structure selected from the group consisting of:

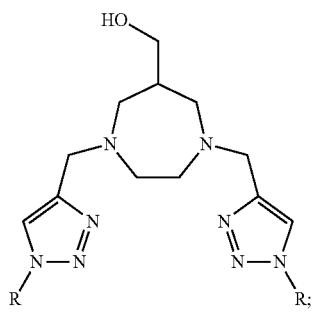

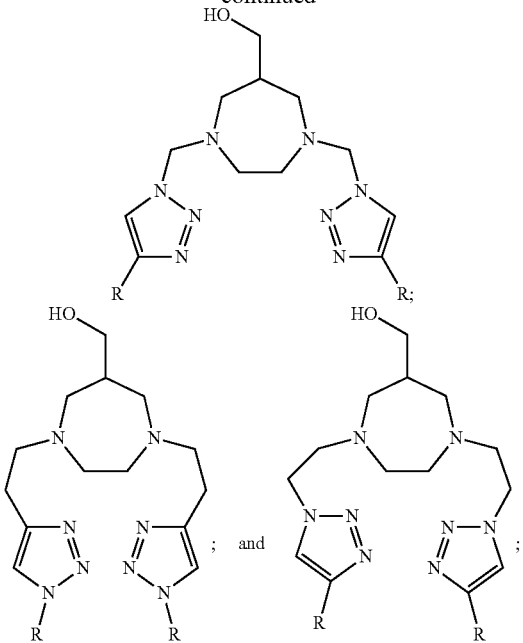

wherein each R is a chemical moiety independently selected from the group consisting of: hydrogen, an electron donating group, an electron withdrawing group, and a solubilizing ligand.

2. The composition of matter as recited in claim 1, comprising at least one $sp^2$ nitrogen atom and at least one sp3 nitrogen atom.

3. The composition of matter as recited in claim 2, wherein the at least one $sp^2$ nitrogen atom and the at least one sp3 nitrogen atom form a central chelating site configured to chelate a metal cation placed in the chelating site.

4. The composition of matter as recited in claim 3, wherein the chelating site comprises two $sp^2$ nitrogen atoms and two $sp^3$ nitrogen atoms.

5. A composition of matter, comprising:
a homopiperazine-based ligand; and
at least one $sp^2$ nitrogen atom and at least one sp3 nitrogen atom; and
wherein the nitrogen atoms form a central chelating site configured to chelate a metal cation placed in the chelating site, the chelating site having a structure

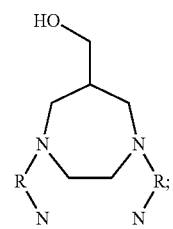

and
wherein —R has a structure selected from: —CH$_2$C—, —CH$_2$N—; —CH$_2$CH$_2$C—; and —CH$_2$CH$_2$N—.

6. The composition of matter as recited in claim 1, comprising a metal cation conjugated with the homopiperazine ligand.

7. The composition of matter as recited in claim 6, comprising a hydroxyl moiety functionalized to the metal cation.

8. The composition of matter as recited in claim 6, wherein the metal cation is selected from the group consisting of: $Cu^{2+}$, $Co^{2+}$, $Fe^{2+}$, and $Ni^{3+}$.

9. The composition of matter as recited in claim 1, wherein
the composition of matter is functionalized on a substrate;
wherein the substrate comprises one or more of a surface and a solid support,
wherein the surface is selected from a group consisting of a planar surface and nanoparticles; and
wherein the solid support is selected from the group consisting of porous beads, a resin, and a filter.

10. The composition of matter as recited in claim 1, wherein at least one of the chemical moieties is the solubilizing ligand; and
wherein the solubilizing ligand comprises polyethlyene glycol.

11. A method of forming the homopiperazine-based ligand as recited in claim 1, the method, comprising:
reacting a homopiperazine-based compound with one or more of an azide and a terminal alkyne in the presence of Cu(I) to form the homopiperazine-based ligand.

12. A method, comprising: neutralizing toxicity of one or more organophosphorus-based compounds by reacting the organophosphorus based compound(s) with a homopiperazine-based ligand-metal complex as recited in claim 6.

13. The method as recited in claim 12, the reacting comprising substituting a leaving group of the organophosphorus-based compound with a hydroxyl moiety conjugated to the homopiperazine-based ligand-metal complex.

14. The composition of matter as recited in claim 6, wherein the metal cation is $Zn^{2+}$.

15. The composition of matter as recited in claim 6, wherein the metal cation is further functionalized to a water molecule.

16. The composition of matter as recited in claim 1, solvated in an aqueous solution in an amount ranging from about 10 mol % to about 50 mol %.

17. The composition of matter as recited in claim 1, solvated in an organic phase solvent in an amount ranging from about 10 mol % to about 50 mol %.

* * * * *